United States Patent [19]

Schnetzinger et al.

[11] Patent Number: 5,071,441

[45] Date of Patent: Dec. 10, 1991

[54] HAIR TREATMENT AND CONDITIONING AGENTS

[75] Inventors: Richard Schnetzinger, Hightstown; Joseph Ciaudelli, Ramsey, both of N.J.

[73] Assignee: Revlon, Inc., New York, N.Y.

[21] Appl. No.: 578,163

[22] Filed: Sep. 6, 1990

Related U.S. Application Data

[62] Division of Ser. No. 254,955, Oct. 7, 1998, Pat. No. 4,973,475.

[51] Int. Cl.$^5$ .................. A61K 7/13; A61K 7/135; A61K 7/06; A61K 7/09
[52] U.S. Cl. ................................. 8/405; 8/406; 424/62; 424/70; 424/71; 424/72
[58] Field of Search ............... 8/405, 406; 424/70, 424/71, 72, 62; 514/773, 788, 772

[56] References Cited

U.S. PATENT DOCUMENTS

| | | | |
|---|---|---|---|
| 2,944,942 | 7/1960 | Charle | 167/87.1 |
| 3,093,146 | 6/1963 | Kalopissis | 132/7 |
| 3,257,449 | 9/1966 | Kalopissis | 260/501 |
| 3,549,602 | 12/1970 | Kalopissis | 260/78 |
| 4,344,763 | 8/1982 | Tolgyesi | 8/127.51 |
| 4,378,345 | 3/1983 | Okumura | 424/45 |
| 4,423,032 | 12/1983 | Abe | 424/70 |
| 4,597,962 | 7/1986 | Grollier | 424/47 |
| 4,919,924 | 4/1990 | Pigiet | 424/72 |

FOREIGN PATENT DOCUMENTS 1199776 6/1967 United Kingdom .

Primary Examiner—A. Lionel Clingman
Assistant Examiner—William S. Parks
Attorney, Agent, or Firm—Julie Blackburn

[57] ABSTRACT

Mercaptyl-containing quaternary nitrogen compounds, which may contain additional functional moieties such as dye, polysiloxane, or polyoxyalkylenes groups, are useful in the treatment of hair, used in hair-treating compositions, to impart properties such as conditioning, shape, color, sheen, and manageability.

2 Claims, No Drawings

HAIR TREATMENT AND CONDITIONING AGENTS

This is a division of copending application Ser. No. 07/254,955 filed on Oct. 7, 1988, now U.S. Pat. No. 4,973,475.

FIELD OF THE INVENTION

This invention relates to mercaptyl-containing chemical compounds, hair-treating compositions, and methods for treating keratinous fiber such as human and other animal hair to impart thereto desired properties such as conditioning, shape, color, sheen and/or manageability.

Hair fiber is principally comprised of keratin, a proteinaceous material which has many alterable chemical characteristics such as net electrical charge and fatty oil content. Such characteristics are related to manageability, body, texture, static behavior, combability and sheen.

It is known that the properties of hair may be altered by contacting hair with surface active agents, salts, and polymers such as polysiloxanes, polyoxyalkylenes and poly(vinylpyrrolidones) and by modifying the chemical structure of the hair's keratin.

The tertiary structure, or three-dimensional shape, of keratin is related to the structure, strength, degree of twist and resilience of hair fiber, and is determined by hydrogen (H—H) and disulfide (S—S) bonds which link adjacent protein chains making up the keratinous fiber. Hydrogen bonding is highly dependent on the moisture content of hair. Therefore, modification of hair shape and body by altering only the hydrogen bonding of keratin achieves only temporary results. On the other hand, the cleavage and recombination of disulfide bonds are not influenced by moisture and are not alterable under normal circumstances. Consequently, hair treatment methods which take advantage of the disulfide bond chemistry of hair are typically considered to produce results of a permanent nature.

Permanent treatments of hair involve the cleavage of keratin disulfide bonds under reducing conditions and the oxidative regeneration of the bonds while the "relaxed" hair is restrained physically by curlers or curling wands or the like. The typical permanent treatment results in the breaking and regeneration of substantially all of the disulfide bonds linking neighboring protein chains. Regeneration of the disulfide bonds at different locations than originally present modifies the tertiary structure of keratin. This influences hair fiber twist and shape.

Another method for imparting permanent properties to hair is to regenerate disulfide bonds not only between protein making up keratin but also between keratin and externally applied mercaptyl-containing compounds.

This invention relates to novel mercaptyl-containing compounds capable of chemically binding to keratinous fiber and methods to impart to human and animal hair desired permanent properties.

Reported Developments

U.S. Pat. Nos. 3,093146 and 3,257,449, both to Kalopissis et al, disclose a hair setting-composition including a mercaptyl-containing ammonium salt of the formula

[HS—CR'H—CON(R)(CH$_2$)$_2$—NHR''R''']$^+$X$^-$

wherein the R radicals are hydrogen or lower alkyl and wherein at least one of the R radicals is a water-repelling fatty acid residue. This patent discloses that the composition may be used to set hair which has not undergone prior disulfide reducing treatment.

U.S. Pat. No. 3,549,602 to Kalopissis et al discloses aqueous alkaline hair-treating compositions including polysulfhydryl polymers formed by the condensation of a polymer-containing anhydride unit with a mercaptoamide amine of the formula R$_1$—NH—(CH$_2$)$_q$—N(R$_3$)—CO—C(R$_2$)H—(CH$_2$)$_p$—SH. The composition is used for permanent hair-setting.

U.K. Patent No. 1,199,776 to McCarty et al discloses a hair-treating composition for setting straight or curled hair including an alkylmercapto group-containing organosilicon polymer of the formula [HS(CH$_2$)$_n$]$_p$Si(R$_m$)(R$_n$)O[—Si(R$_2$″)O—]$_x$—[—Si(R″)((CH$_2$)$_n$—SH)—O—]$_y$[—Si(R)(R″)—O—]$_z$-[—Si(R$_m$)(R″)$_{3-(m+p)}$)-]-[—(CH$_2$)$_n$SH]$_p$. This patent discloses that the mercaptyl groups bond chemically to hair keratin thereby attaching the silicon polymer chains to the hair and providing long term protection against the deleterious effects of humidity.

The compounds, compositions and methods of the present invention are described below.

SUMMARY OF THE INVENTION

This invention relates to mercaptyl-containing quaternary nitrogen compounds which are useful for the treatment of keratinous fiber. Exemplary compounds of this invention are described by Formula I below.

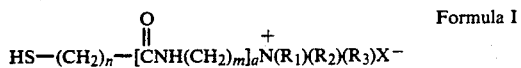

Formula I wherein:
a is 0 or 1;
m and n are each independently about 1 to about 20;
R$_1$ is alkyl;
R$_2$ is alkyl or a moiety which under oxidizing conditions is capable of imparting color to hair;
R$_3$ is alkyl, hydroxy alkyl, dihydroxy alkyl, hydroxy polyoxyalkylene alkyl, fatty alkyl, or a silicon-containing substituent of the formula

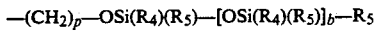

wherein:
b is about 1 to about 25;
p is about 1 to about 14; and
R$_4$ and R$_5$ are each independently lower alkyl, phenyl, phenyl lower alkyl, styryl or —O—Si(R$_6$)(R$_7$)(R$_8$), with
R$_6$, R$_7$, and R$_8$ each being independently lower alkyl; and
X is a nontoxic anion.

This invention relates also to keratinous fiber-treating compositions including a mercaptyl-containing quaternary nitrogen compound, for example, a compound according to Formula I above.

This invention relates further to methods for treating keratinous fiber to impart desired permanent properties thereto including contacting said fiber with a composition comprising a mercaptyl-containing quaternary nitrogen compound. The present invention can be used to impart permanent "conditioning" properties, as well as other desired properties discussed in more detail below, to keratinous fiber treated with a mercaptyl-containing quaternary nitrogen compound of this invention.

DETAILED DESCRIPTION

This portion of the application includes sections entitled, Definitions, Compounds and their Methods of Preparation, and Hair-Treating Methods and Compositions.

Definitions

The term "conditioning", as it applies to keratinous fiber such as hair, denotes textural properties of smoothness, softness, combability and the absence of static buildup. Other properties recognized as characteristic of "conditioning" are known to those skilled in the art.

The term "alkyl" means an aliphatic hydrocarbon including about one to about eight carbon atoms in the chain which can be either straight or branched. The preferred alkyl groups are lower alkyl groups which include about one to about four carbon atoms.

The term "fatty alkyl" means an aliphatic hydrocarbon group including about eleven to about twenty two carbon atoms in the chain which can be either straight or branched.

The term "mercaptyl" means an HS- group.

The term "reducing agent" means a material which provides a source of electrons or hydrogen. In the context of the present invention, a reducing agent permits the cleavage of disulfide bonds in keratinous fiber to form mercaptyl groups.

The term "oxidizing agent" means a material which promotes the oxidative bonding of mercaptyl groups to form disulfide bonds. Exemplary oxidizing agents include hydrogen peroxide and sodium bromate.

$X^-$ is an anion that is non-toxic to human and animal skin and scalp. Preferred anions include chloride, bromide, sulfate, bicarbonate, acetate, lactate, and phosphate.

The compounds, methods for their preparation and examples of the preparation of specific compounds of this invention are described in the next section.

Compounds and Methdos for Their Preparation

A class of compounds of Formula I, which is of particular use in the hair-dyeing method described in more detail below, comprises compounds where $R_2$ is a substituent group which is capable of exhibiting a visible color chromophore in oxidized form and thereby capable of imparting color to hair. A particularly preferred hair-coloring moiety has the formula $$Z-(NR_9)_c-CH_2CH_2-$$

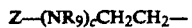

wherein: c is 0 or 1; $R_9$ is hydrogen, phenyl, lower alkyl or hydroxy lower alkyl; and Z is phenyl substituted by one or more substituents selected from the group including amino, alkylamino, phenylamino, hydroxyalkyl, hydroxy, chloro, methoxy and nitro. A most preferred class of substituent groups include a $Z-(NR_9)c$ moiety which may be described as 4-aminoanilino, 2-methyl-5-aminoanilino, 3-methyl-4-aminoanilino, m-,o- and p-hydroxyanilino, 4-nitro-2-aminoaniline, 4-chloro-2-aminoaniline, 2-aminoanilino, 2-chloro-4-aminoanilino, 4-amino-2-chloro-5-methoxyanilino, 4-amino-N-phenylanilino, 4-amino-3-nitro-N-phenylanilino, 4-amino-N-methylanilino, 4-amino-2,6-dichloroanilino, 4-amino-2-nitroanilino, 4-(bis-2-hydroxyethyl)amine-2-nitro-N-methylanilino, 4-(bis-2-hydroxyethyl)amine-2-nitro-N-(2-hydroxyethyl)anilino, 4-amino-2-nitro-N-(2-hydroxyethyl)anilino, 2-nitro-N-(2-hydroxyethyl)anilino, 2-amino-4-nitro-N-[tris(hydroxymethyl)methyl]anilino, and 2-amino-4-nitro-N-(2-hydroxyethyl)-anilino, when c is 1, and phenyl-2,5-diamine, phenyl-3,4-diamine, catechol, pyrogallol or resorcinol when c is 0.

Other classes of compounds within the scope of Formula I, which are particularly useful for imparting additional permanent properties, such as sheen and lubricity properties, to hair treated therewith according to the method of this invention, comprise compounds wherein $R_3$ is:

(A) a silicon-containing substituent of the formula $$-(CH_2)_p-OSi(R_4)(R_5)-[OSi(R_4)(R_5)]_b-R_5$$

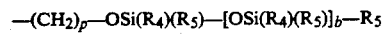

and, wherein:

b is about 1 to about 25;

p is about 1 to about 14; and $R_4$ and $R_5$ are each independently lower alkyl, phenyl, phenyl lower alkyl, styryl or $-O-Si(R_6)(R_7)(R_8)$; and $R_6$, $R_7$, and $R_8$ are each independently lower alkyl; and (B) $R_3$ is hydroxy polyoxyalkylene alkyl of the formula $$-(CH_2)_d-(OC_nH_{2n})_e-OH$$

and wherein:

d is about 1 to about 12;

n is 2 or 3; and e is about 1 to about 20.

Compounds according to the present invention may be prepared by the reaction of an N-alkylation agent with an appropriate amine intermediate containing a mercaptyl group. A preferred method involves the N-alkylation of a tertiary amine intermediate. Compounds of Formula I where a is 1, which are particularly preferred in view of the increased stability of the amido functionality, may be prepared using an intermediate which is the product of a mercaptyl-containing carboxylic acid or -carboxylic ester and an N-aminoalkyl tertiary amine reacted under appropriate amide-forming or ester-amide interchange conditions. This reaction sequence is depicted in Scheme I below.

Scheme I

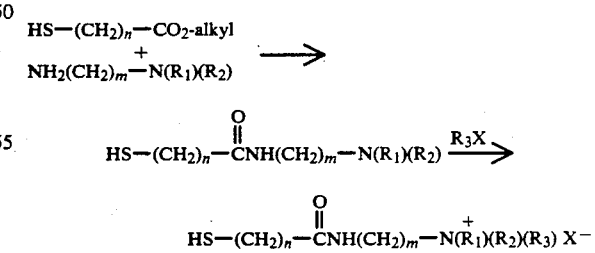

wherein the variables m, n, a, $R_1$, $R_2$, $R_3$ are as defined for Formula I above.

Diamino compounds shown in Scheme I above are available commercially or may be prepared according to methods known in the literature. Compounds including $R_1$ and/or $R_2$ substiutent groups other than hydrogen may be prepared by selectively N-alkylating the unsubstituted diamine or by reducing the analogous nitro compound. N-alklating agents may include compounds such as alkyl halides or sulfonates, and such agents wherein the alkyl group is substituted with a polysiloxy or polyalkyloxy group.

Mercaptyl-containing compounds shown in Scheme I above are available commercially or may be may be prepared according to known literature methods.

Compounds of Formula I where a is 0 may be prepared also by the N-alkylation of a tertiary amine intermediate which is the product of a secondary amine and a mercaptylalkyl halide. Another means for preparing these compounds which does not include the amido functionality involves the reaction of an appropriate alkyl mercaptyl reagent, such as a mercaptyl-containing alkyl halide, with a tertiary amine. This reaction sequence, shown in Scheme II below, is also an alternative route to the preparation of the amido-containing compounds, where an appropriate tertiary amine is reacted with an N-alkylating amidomer-captyl-containing compound.

SCHEME II

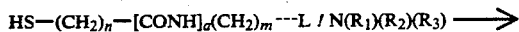

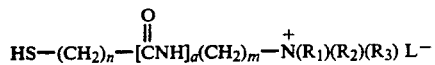

where L is a leaving group such as bromo, chloro, sulfonate, and m, n, a, $R_1$, $R_2$, $R_3$ are as defined above.

The following examples are illustrative of the preparation of the compounds of the invention.

EXAMPLE 1

The Preparation of
N-Dimethyl-N-Ethyl-N-[3-(2-Mercaptoacetamide)-propyl]ammonium Bromide A mixture of 3-Dimethylaminopropylamine (60 g) and Ⓡthyl thioglycolate (60 g) in methanol (125 ml) is stirred at RT for one hour. Bromoethane (60 g) is added to the stirred mixture which is refluxed for 1.5 hours. The methanol in the reaction mixture is distilled away leaving the desired product as an oily residue. IR spectra(neat)(cm$^{-1}$): 3420(s), 3240(s), 2960(s), (m), 2510(w), 2480(w), 1710(s), 1540(s), 1465(s).

EXAMPLE 2

The Preparation of
N-Trimethyl-N-[3-(2-Mercaptoacetamide)propyl]ammonium Bromide A mixture of 3-Dimethylaminopropylamine (30 g) and ethyl thioglycolate (30 g) in methanol (60 ml) is stirred at RT for 1.5 hours. Methyl iodide (80 g) is added to the stirred mixture which is refluxed for 2 hours. The methanol in the reaction 1.5 mixture is removed under vacuo leaving 106 g of the desired product as an oil. IR spectra(neat)(cm$^{-1}$): 3440(s), 3260(s), 2960(bs), 2700(s), 2510(w), 2460(W), 1725(m), 1650(s), 1540(s), 1480(s).

EXAMPLE 3

The Preparation of
N-Dimethyl-N-Dodecyl-N-[3(2-Mercaptoacetamide)p-rpyl]ammonium Bromide A mixture of 3-Dimethylaminopropylamine (30 g) and ethyl thioglycolate (30 g) in methanol (60 ml) is stirred at RT for 4 hours. The methanol is removed under vacuo and toluene (85 g) and 1-bromododecane (80 g) are added to the residue. The reaction mixture is refluxed for about three hours and the toluene is removed under vacuo. The resulting desired product solidified slowly to a yellow waxy material. IR spectra(neat) (cm$^{-1}$): 3420(m), 3240(s), 2920(bs), 2680(s), 2510(w), 2470(w), 1725(W), 1665(s), 1645(s), 1540(s), 1465(s).

EXAMPLE 4

The Preparation of
N-Trimethyl-N-[3-(2-Mercaptoacetamide)propyl]ammonium Iodide

A mixture of 3-dimethylaminopropylamine (70 g) and methyl 3-mercaptopropionate (60 g) is stirred under vacuum at temperature of about 85° C. for about three hours. The reaction residue comprises the amide intermediate. IR spectra(neat)(cm$^{-1}$): 3290(s), 3075(m), 2940(s), 2860(s), 2810(s), 2760(s), 2580–2400(w), 1690(s), 1575(s), 1460(s). Ethyl bromide (23 g) in toluene is added to about 30 grams of the reaction mixture residue and the mixture is refluxed, the toluene removed under vacuum, and the desired product obtained as an oil.

Mercaptyl-containing quaternary nitrogen compounds described above may be used in the hair treating methods and the hair treating compositions described below.

Hair Treating Methods and Compositions

The compounds of the present invention can be used to impart permanent conditioning and shaping, for example, curling or straightening, to keratinous fiber. The permanent conditioning properties are believed to result from the chemical binding of the quaternary group derived from the mercaptyl-containing quaternary nitrogen compound of Formula I to keratin by means of disulfide bonds. Such bonded chemical groups remain on the hair keratin and are not removed by shampooing. Of course., as new hair grows from the scalp, hair fiber which is not chemically bound to compounds of Formula I will diminish the conditioning properties achieved by the present invention. Accordingly, it should be understood that periodic treatment of hair with a compound of the present invention will be required to maintain the permanent conditioning effect.

One aspect of the present invention comprises contacting hair with a reducing agent followed by the mercaptyl-containing quaternary nitrogen compound and an oxidizing agent. The reducing agent can either remain on the hair or be rinsed from the hair prior to the application of the mercaptyl-containing quaternary compound.

Reducing agents and reducing compositions, which are known to persons skilled in the art, can be used. The reducing agent is applied typically to the hair in the form of an aqueous composition including, for example, ammonium monothioglycolate or glyceryl monothioglycolate, for a time which is effective for reducing a substantial number of disulfide bonds. Typical times are from about 5 to about 20 minutes at temperatures of about room temperature to about 110° F.

Oxidizing conditions which are known to persons skilled in the art may be used in the present method of hair treatment. The oxidizing conditions may involve exposure to atmospheric or concentrated oxygen or result from the application of a fluid composition including an oxidizing agent to the hair. The oxidizing agent is chosen from those used typically in the art such as hydrogen peroxide and sodium bromate. It is applied preferably in the form of aqueous solutions and is allowed to remain on the hair for a time which is effective to regenerate a substantial number of the reduced disulfide bonds. Typical application times are from about 5 to about 20 minutes at temperatures from room temperature to about 110° F. The oxidizing agent is rinsed from the hair using tap water or a rinse product known to the art. A preferred rinse composition comprises an acidic aqueous composition having a pH of about 4.5 to about 6.5.

Another aspect of the present development is a method for permanently conditioning and shaping hair comprising the steps of:

(1) contacting hair with an aqueous composition comprising a compound according to Formula I above in the presence of a mercaptyl-disulfide interchange catalyst; and (2) subjecting hair contacted with said composition to oxidizing conditions.

The mercaptyl-disulfide interchange catalyst is a material which, in the presence of protein disulfide groups and free non-protein mercaptyl groups, will promote the cleavage of the disulfide bonds and permit the recombination of protein mercaptyl groups and free mercaptyl groups to form disulfide bonds which link protein and non-protein mercaptyl compounds. One such catalyst is thioredoxin, which is an enzyme protein. U.S. Pat. No. 4,738,841 disclosed thioredoxin and equivalent enzymes. The concentration of thioredoxin in the composition is about 1 nmole/ml to about 100 nmole/ml.

Although the compound of formula I contains free mercaptyl groups which may participate in the reduction of the disulfide bonds to free mercaptyl groups, it is preferred that the composition in the foregoing method containing an additional source of reducing material such as described herein above. The most preferred materials include glyceryl monothioglycolate and bisulfite salts such as sodium, potassium and ammonium bisulfite.

The mercaptyl-disulfide catalyst and quaternary compound are permitted to remain on the hair for an amount of time sufficient to cleave a substantial amount of the disulfide bonds in the hair. A preferred time is about 2 to about 15 minutes at a temperature from room temperature to about 90° F.

It is preferred that this method be practiced by subjecting hair treated according to step (1) to oxidizing conditions as described above prior to rinsing the mercaptyl-containing quaternary nitrogen compound from the hair. It is believed that this improves the opportunity for the mercaptyl-containing quaternary nitrogen compound to participate in the disulfide formation and thereby chemically bind to keratin.

The present invention may also be used to impart other permanent properties, for example, sheen, water and humidity resistance and/or color, to treated keratinous fiber by the suitable choice of a compound of Formula I having particular substituent groups as described herein and/or use of special embodiments of the present method.

One such embodiment relates to the dyeing of keratinous fiber, wherein the dye-complexing properties of the quaternary nitrogen compounds of Formula I are exploited. This involves introducing the quaternary nitrogen group into the chemical structure of the keratinous fiber by contacting said fiber with a composition containing a mercaptyl-containing quaternary nitrogen compound, subjecting such fiber to oxidizing conditions and contacting fiber containing the chemically bound quaternary groups with a hair dye capable of complexing with the quaternary moiety. Exemplary dyes that can be used in this method include Disperse Black 9, Disperse Blue 3, Direct Red 81, and Acid Red 95.

A further embodiment of the method aspects of the present invention relates to the permanent dyeing of keratinous fiber comprising the steps of:

(1) contacting said fiber with a composition containing a mercaptyl-containing quaternary nitrogen compound which also contains a moiety capable of imparting color to said fiber under oxidizing conditions; and (2) subjecting fiber treated according to step (1) to oxidizin conditions.

Another aspect of the present invention encompasses a hairtreating composition comprising a mercaptyl-containing quaternary nitrogen compound of Formula I. The composition can be aqueous or nonaqueous and be in the form of a solution, a gel or a concentrate which can be mixed shortly prior to use. Preferred compositions are aqueous and may include also nonaqueous fluid materials which are soluble, miscible or dispersible in water and which are generally recognized as nontoxic to skin and scalp. Exemplary materials include ethanol, isopropanol, butanol, benzyl alcohol and other co-solvents, and propellant gases such as carbon dioxide, nitrous oxide, and fluorinated and/or chlorinated hydrocarbons. The amounts of the additional fluid materials included in the compositions of this development can be determined by those skilled in the art and can vary depending on the composition's intended use.

The mercaptyl-containing compound is present in the composition in an amount which depends also on the composition's intended use and which is effective to impart to keratinous fiber the desired properties. Typical amounts of compound will be about 0.1 to about 30 weight percent based on the total weight of the composition. In compositions used for the permanent waving of hair into tight curls, the mercaptyl-containing compound comprises about 5 to about 30 weight percent based on the total weight of the composition. In compositions where only permanent conditioning properties are to be imparted to the hair, the mercaptyl-containing compound comprises about 0.1 to about 2 weight percent based on the total weight of the composition. In compositions where a dye complex is formed with the quaternary compound, the mercaptyl-containing compound may comprise 0.1 to 15 weight percent of the composition. The preferred amount of quaternary compound included in a dye composition will be up to the formulist who will determine a particular dye system specific for a particular desired type and color of hair.

A particularly preferred composition includes also a mercaptyl-disulfide bond interchange catalyst, which can be thioredoxin or analogue thereof. The concentration of thioredoxin in the composition is about 1 to about 100 nmole/ml. A preferred concentration is about 5 to about 25 nmole/ml of composition.

A most preferred composition includes also a reducing agent such as glyceryl monothioglycolate or a bisulfite salt. The reducing agent may comprise about 1 to about 20 percent of the total weight of the composition. A preferred amount of reducing agent is about 2 to about 8 weight percent of the composition.

It should be understood that the formulation of the present composition into a commercially acceptable composition may involve the inclusion of additional optional ingredients such as fragrances, thickeners, preservatives, stabilizers, emulsifiers, the nature and amounts of which are within the skill of the art.

The following examples illustrate the practice of hair treating methods of the present invention.

Examples of Hair Treating Methods

The hair treated in Examples 6 to 9 comprise tresses of dark brown virgin human hair (11 inches in length).

EXAMPLE 6

A hair tress is wrapped on a curling rod which is submerged for 20 mins at 50° C. in an aqueous solution having a pH of about 9 and containing 5% of the mercapto-quaternary compound of Example 1 above. The hair is removed from the solution, damp dried, submerged at RT in a 10% aqueous solution of sodium bromate (pH of 6) for 5 mins, removed from the solution, shampooed twice and air dried.

EXAMPLE 7

A hair tress is wrapped on a curling rod and is treated with an aqueous solution of glyceryl monothioglycolate (GMTG). The hair is removed from the solution, damp dried and submerged in an aqueous solution of the mercapto-quaternary compound of Example 1 above for 20 mins. The hair is removed from the solution, damp dried without a rinse and submerged at RT in a 10% solution (pH of 6) of sodium bromate for 5 mins. The hair is rinsed free of bromate solution, shampooed twice and air dried.

EXAMPLE 8

A hair tress wrapped on a curling rod is submerged for 20 mins at 50° C. in a shaken composition containing 30 ml of a 5% aqueous solution of the mercapto-quaternary compound of Example 1 above, sodium bisulfite (5 g), butanol (20 ml), ethyl alcohol (25 ml) and water (25 ml). The hair is removed from the composition, damp dried without a rinse and submerged for 5 min in a neutralizing solution containing 10% sodium bromate in a mixture of water:ethanol:butanol (50:25:25). The hair is rinsed free of bromate solution, shampooed twice and air dried.

Comparative Example C-1

A tress of hair was treated according to the procedure described in Example 6 except that GMTG was used as control.

After drying, the hair treated according to each of the aforementioned examples is unwound from the curling rods and the curl-length, curl pattern and softness of the hair is evaluated. The results are presented below.

| Example No. | Hair Length | Hair turns | Comment |
|---|---|---|---|
| Untreated | 11 in. | | |
| 6 | 8 in. | 1½ | very soft curl |
| 7 | 4 in. | | |
| 8 | 6 in. | 4 | |
| C-1 | 2 in. | 6½ | very tight curl |

The procedures of the aforementioned examples are repeated using virgin blond hair, and the treated hair is submerged in a 0.1% aqueous solution (pH of 6) Brilliant Vital Red dye for 15 min. at RT, rinsed under running tap water, shampooed twice with ammonium lauryl sulfate solution, washed with methanol, washed with DMSO, rinsed under water, and washed again with DMSO.

The color density of the treated hair is measured on a relative scale and the results are presented below.

| Example No. | Observation | Color intensity |
|---|---|---|
| No treatment | No color | 0 |
| C-1' | Very slight color | 0.5 |
| 6' | Slightly more color | 1.5 |
| 7' | Some Color | 2 |
| 8' | Most Color | 5 |

The results of the aforementioned examples demonstrate that hair treated with the mercapto-containing quaternary compound of Formula I is chemically bonded thereto and has imparted thereto permanent conditioning properties. The test results demonstrate also that hair treated with the quaternary compounds of this invention are capable of permanently complexing significant amounts of dye even after shampoo treatment.

We claim:

1. A hair-treating composition comprising an effective hair-treating amount of a mercapto-containing quaternary nitrogen compound.

2. A composition according to claim 1 including an effective catalytic amount of a mercaptyl-disulfide interchange catalyst.

* * * * *